United States Patent
Yu et al.

(10) Patent No.: US 10,005,723 B2
(45) Date of Patent: Jun. 26, 2018

(54) PROCESS TO PRODUCE POLYCARBAMATE, POLYCARBAMATE PRODUCED THEREBY AND A COATING COMPOSITION COMPRISING THE POLYCARBAMATE

(71) Applicant: Dow Global Technologies LLC, Midland, MI (US)

(72) Inventors: Xinrui Yu, Midland, MI (US); Yiyong He, Midland, MI (US); John W. Hull, Jr., Midland, MI (US); Daryoosh Beigzadeh, Midland, MI (US); Duane Romer, Midland, MI (US); Thomas Clark, Midland, MI (US); Peter Margl, Midland, MI (US); Congcong Lu, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days. days.

(21) Appl. No.: 14/912,157

(22) PCT Filed: Aug. 15, 2014

(86) PCT No.: PCT/US2014/051174
§ 371 (c)(1),
(2) Date: Feb. 15, 2016

(87) PCT Pub. No.: WO2015/023905
PCT Pub. Date: Feb. 19, 2015

(65) Prior Publication Data
US 2016/0185713 A1    Jun. 30, 2016

Related U.S. Application Data

(60) Provisional application No. 61/866,075, filed on Aug. 15, 2013.

(51) Int. Cl.
| | | |
|---|---|---|
| *C07C 271/00* | (2006.01) | |
| *C07C 269/00* | (2006.01) | |
| *C08G 65/333* | (2006.01) | |
| *C08G 71/04* | (2006.01) | |
| *C07C 271/10* | (2006.01) | |
| *C09D 7/12* | (2006.01) | |
| *C09D 175/04* | (2006.01) | |
| *C09D 7/63* | (2018.01) | |

(52) U.S. Cl.
CPC .......... *C07C 269/00* (2013.01); *C07C 271/10* (2013.01); *C08G 65/33303* (2013.01); *C08G 65/33324* (2013.01); *C08G 71/04* (2013.01); *C09D 7/1233* (2013.01); *C09D 7/63* (2018.01); *C09D 175/04* (2013.01)

(58) Field of Classification Search
None
See application file for complete search history.

(56) References Cited

U.S. PATENT DOCUMENTS

| | | | |
|---|---|---|---|
| 4,443,622 A | 4/1984 | Smith | |
| 5,719,237 A | 2/1998 | Rehfuss et al. | |
| 2007/0252106 A1* | 11/2007 | Buchold | ................. C07C 68/00 252/182.3 |
| 2008/0076843 A1* | 3/2008 | Clark | ................. C08G 18/3893 521/137 |

FOREIGN PATENT DOCUMENTS

| | | |
|---|---|---|
| DE | 10341952 | 5/2005 |
| EP | 0581131 | 2/1994 |
| WO | WO93/04106 | 3/1993 |
| WO | WO2008/036365 | 3/2008 |
| WO | WO2009/025703 | 2/2009 |

OTHER PUBLICATIONS

PCT Search Report dated Oct. 30, 2014; from PCT counterpart Application No. PCT/US2014/051174.
PCT IPRP dated Feb. 16, 2016; from PCT counterpart Application No. PCT/US2014/051174.
EP Office Action dated Mar. 24, 2015; from EP counterpart Application No. 14755958.7.
EP Response to Office Action dated Sep. 20, 2016; from EP counterpart Application No. 14755958.7.
PCT Search Report dated Oct. 31, 2014; from PCT counterpart Application No. PCT/US2014/051175.
PCT IPRP dated Feb. 16, 2016; from PCT counterpart Application No. PCT/US2014/051175.
EP Office Action dated Mar. 23, 2015; from EP counterpart Application No. 14755959.5.
John Wiley & Sons, et al., "Supermolecular Chemistry, Urea and Thiourea Clathrates", Supermolcular Chemistry 2007, vol. 19 pp. 393-398.
Kenneth D. M. Harris, "Fundamental and Applied Aspects of Urea and Thiourea Inclusion Compounds", Supermolcular Chemistry 2007, vol. 19, pp. 47-53.
Woods, G., The ICI Polyurethenes Book, 2nd ed. (ICI Polyurethenes, Netherlands, 1990).
Chinese Office Action dated Aug. 8, 2017; from Chinese counterpart Application No. 201480043106.8.

(Continued)

*Primary Examiner* — Sudhakar Katakam
*Assistant Examiner* — Ana Z Muresan

(57) ABSTRACT

A process to prepare polycarbamate comprising adding urea to a polyol in the presence of at least one catalyst selected from the group consisting of compounds having the following formula $M_m Z_n$; wherein M is a trivalent metal, and Z is an anionic functionality or a functionality capable of forming a covalent bond with M and wherein n times a valence number of Z equals X and m times three equals Y wherein the absolute value of X equals the absolute value of Y is provided. Also provided are a polycarbamate produced according to the process and a coating composition comprising the polycarbamate.

3 Claims, No Drawings

(56) References Cited

OTHER PUBLICATIONS

Japanese Office Action dated Mar. 23, 2018; from Japanese counterpart Application No. 2016-534852.

* cited by examiner

PROCESS TO PRODUCE POLYCARBAMATE, POLYCARBAMATE PRODUCED THEREBY AND A COATING COMPOSITION COMPRISING THE POLYCARBAMATE

FIELD OF INVENTION

The instant invention relates to a process to produce polycarbamate, polycarbamate produced thereby and a coating composition comprising polycarbamate.

BACKGROUND OF THE INVENTION

One of the widely used class of catalysts for the reaction of polyols with amides or esters is tin-based catalysts. However, tin-based materials are now banned in coating materials in some regions such as Europe. Alternative catalysts for the reaction of polyols with amides or esters would therefore be desirable.

SUMMARY OF THE INVENTION

The instant invention is a process to produce polycarbamate, polycarbamate produced thereby and a coating composition comprising polycarbamate.

The process according to the present invention comprises adding urea to a polyol in the presence of at least one catalyst selected from the group consisting of: (i) compounds having the following formula $M_m Z_n$; wherein M is a trivalent metal, and Z is an anionic functionality or a functionality capable of forming a covalent bond with M and wherein n times a valence number of Z equals X and m times three equals Y wherein the absolute value of X equals the absolute value of Y.

DETAILED DESCRIPTION OF THE INVENTION

The instant invention is a process to produce polycarbamate, polycarbamate produced thereby and a coating composition comprising polycarbamate.

The process according to the present invention comprises adding urea to a polyol in the presence of at least one catalyst selected from the group consisting of: (i) compounds having the following formula $M_m Z_n$; wherein M is a trivalent metal, and Z is an anionic functionality or a functionality capable of forming a covalent bond with M and wherein n times a valence number of Z equals X and m times three equals Y wherein the absolute value of X equals the absolute value of Y.

In an alternative embodiment, the instant invention further provides a polycarbamate produced according to any embodiment of the inventive process disclosed herein.

In another alternative embodiment, the instant invention further provides a coating composition comprising the polycarbamate according to any of the embodiments disclosed herein.

Urea

In embodiments of the process, the urea may be added in either solid or liquid form. In a specific embodiment, the urea is added in liquid form.

The liquid form of the urea (or "liquid urea") may be achieved in any acceptable manner. For example, the urea may be dissolved in a first solvent. Alternatively, the urea may be melted. In yet another alternative, the urea may be suspended in a clathrate. A urea clathrate may also be known as a urea inclusion compound and may have the structure as described in "Supramolecular Chemistry" John Wiley & Sons, Jonathan w. Steed, Jerry L. Atwood, pp. 393-398 and Harris, K. D. M., "Fundamental and Applied Aspects of Urea and Thiourea Inclusion Compounds", Supramol. Chem. 2007, 19, 47-53.

The liquid form of the urea may alternatively be present in a combination of liquid forms.

In a particular embodiment, the urea is dissolved in water. In another embodiment, the urea may be dissolved in a mixture of two or more first solvents. Such first solvents include organic solvents. In an alternative embodiment, the urea is dissolved in one or more first solvents selected from water and organic alcohols. In one embodiment, urea is partially soluble in the first solvent or mixture of first solvents. In yet another embodiment, urea is fully soluble in the first solvent or mixture of first solvents.

Polyol

As used herein, the term "polyol" means an organic molecule having at least 2 —OH functionalities. As used herein, the term "polyester polyol" means a subclass of polyol that is an organic molecule having at least 2 alcohol (—OH) groups and at least one carboxylic ester ($CO_2$—C) functionality. The term "alkyd" means a subclass of polyester polyol that is a fatty acid-modified polyester polyol wherein at least one carboxylic ester functionality is preferably derived from an esterification reaction between an alcoholic —OH of the polyol and a carboxyl of a ($C_8$-$C_{60}$) fatty acid. The polyol may be any polyol; for example, the polyol may be selected from the group consisting of acrylic, styrene-acrylic, styrene-butadiene, saturated polyester, polyalkylene polyols, urethane, alkyd, polyether or polycarbonate. In one exemplary embodiment, the polyol component comprises hydroxyethyl acrylate. In another exemplary embodiment, the polyol component comprises hydroxyethyl methacrylate.

The reaction mixture may comprise from 10 to 100 percent by weight of polyol; for example, from 30 to 70 percent by weight of polyol. In one embodiment, the polyol has a functional structure of a 1,2-diol, 1,3-diol, or combinations thereof.

The polyol can be non-cyclic, straight or branched; cyclic and nonaromatic; cyclic and aromatic, or a combination thereof. In some embodiments the polyol comprises one or more non-cyclic, straight or branched polyols. For example, the polyol may consist essentially of one or more non-cyclic, straight or branched polyols.

In one embodiment, the polyol consists essentially of carbon, hydrogen, and oxygen atoms. In another embodiment, the polyol consists of primary hydroxyl groups. In yet another embodiment, the hydroxyl groups are in the 1,2 and/or 1,3 configuration. Exemplary polyol structures are shown below for illustrative purposes.

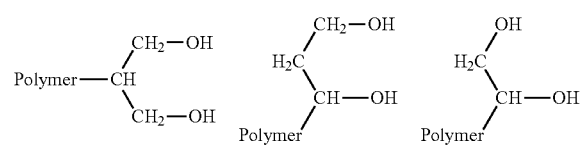

Polyol useful in embodiments of the inventive process include oligomers or polymers derived from hydroxy-containing acrylic monomeric units. Suitable monomers may be, but are not limited to, hydroxyethyl acrylate, hydroxypropyl acrylate, hydroxybutyl acrylate, hydroxydodecyl acrylate, hydroxyethyl methacrylate, hydroxypropyl methacrylate, hydroxybutyl methacrylate, hydroxydodecyl methacrylate, hydroxybutyl vinyl ether, diethylene glycol vinyl ether and a combinations thereof. The polyol useful in embodiments may be prepared by reacting at least one hydroxyl-containing monomer with one or more monomers. Suitable monomers may be, but are not limited to, vinyl monomers such as styrene, vinyl ether, such as ethyl vinyl ether, butyl vinyl ether, cyclohexyl vinyl ether, ester of unsaturated carbonic acid and dicarbonic acid, such as methyl acrylate, methyl methacrylate, ethyl acrylate, ethyl methacrylate, 2-ethylhexyl acrylate, 2-ethylhexyl methacrylate, dodecyl acrylate, dodecyl methacrylate, dimethyl maleate and a mixture thereof.

Polyols useful in certain embodiments of the inventive process include polyether polyols and polyester polyols. Suitable polyols include, for example, ethylene glycol, diethylene glycol, neopentyl glycol, 1,4-butanediol, 1,6-hexanediol, glycerol, pentaerythritol, sorbitol and mannitol. Suitable glycols thus include ethylene glycol, propylene glycol, diethylene glycol, triethylene glycol, tetraethylene glycol, pentaethylene glycol, hexaethylene glycol, heptaethylene glycol, octaethylene glycol, nonaethylene glycol, decaethylene glycol, neopentyl glycol, glycerol, 1,3-propanediol, 2,4-dimethyl-2-ethyl-hexane-1,3-diol, 2,2-dimethyl-1,2-propanediol, 2-ethyl-2-butyl-1,3-propanediol, 2-ethyl-2-isobutyl-1,3-propanediol, 1,3-butanediol, 1,4-butanediol, 1,5-pentanediol, 1,6-hexanediol, 2,2,4-tetramethyl-1,6-hexanediol, thiodiethanol, 1,2-cyclohexanedimethanol, 1,3-cyclohexanedimethanol, 1,4-cyclohexanedimethanol, 2,2,4-trimethyl-1,3-pentanediol, 2,2,4-tetramethyl-1,3-cyclobutanediol, p-xylenediol, hydroxypivalyl hydroxypivalate, 1,10-decanediol, hydrogenated bisphenol A, trimethylolpropane, trimethylolethane, pentaerythritol, erythritol, threitol, dipentaerythritol, sorbitol, mannitol, glycerine, dimethylolpropionic acid, and the like.

Polycarboxylic acids useful in the invention may include, but are not limited to, phthalic anhydride or acid, maleic anhydride or acid, fumaric acid, isophthalic acid, succinic anhydride or acid, adipic acid, azeleic acid, and sebacic acid, terephthalic acid, tetrachlorophthalic anhydride, tetrahydrophthalic anhydride, dodecanedioic acid, sebacic acid, azelaic acid, 1,4-cyclohexanedicarboxylic acid, 1,3-cyclohexanedicarboxylic acid, 2,6-naphthalenedicarboxylic acid, glutaric acid, trimellitic anhydride or acid, citric acid, pyromellitic dianhydride or acid, trimesic acid, sodium sulfoisophthalic acid, as well as from anhydrides of such acids, and esters thereof, where they exist. Optionally monocarboxylic acids may be employed including, but not limited to, benzoic acid. The reaction mixture for producing alkyds includes one or more aliphatic or aromatic polycarboxylic acids, esterified polymerization products thereof, and combinations thereof. As used herein, the term "polycarboxylic acid" includes both polycarboxylic acids and anhydrides thereof. Examples of suitable polycarboxylic acids for use in the present invention include phthalic acid, isophthalic acid, terephthalic acid, tetrahydrophthalic acid, naphthalene dicarboxylic acid, and anhydrides and combinations thereof.

Addition Step

The addition of the urea to polyol may be accomplished by any means. In a particular embodiment of the process, the adding the urea to the polyol is conducted in a batch manner. In a particular embodiment of the process, the adding the urea to the polyol is conducted in a semi-batch manner. In one embodiment, the urea is added at a constant rate over a period of time in which the reaction proceeds. In yet another embodiment, the urea is added to the polyol at more than one rate, with the rate changing over the time period in which the reaction proceeds. In yet another embodiment, the urea is added to the polyol using a pulsed constant rate in which the urea is added at a rate for a first period of time, followed by a second period of no urea addition, followed by urea addition at the same rate for a third period of time, and so on. In another alternative embodiment, the urea in liquid form is added to the polyol using a pulsed variable rate in which the urea is added at a first rate for a first period of time, followed by a second period of no urea addition, followed by urea addition at a second rate for a third period of time, and so on.

In one embodiment of the process, the polyol is complete polyol in the absence of any solvent. In an alternative embodiment of the process, the polyol is dissolved in a second solvent prior to the adding the urea to the dissolved polyol. The second solvent may be any solvent or mixture of solvents in which the polyol is soluble or partially soluble. In certain embodiments, the first and second solvents form a heterogeneous azeotrope allowing removal of the first solvent by decantation or other means. In certain embodiments, removal of the first solvent from a heterogenous azeotrope permits concurrent removal of certain by-products, such as ammonia, which are soluble in the first solvent. In yet an alternative embodiment, the first and second solvents form a heterogeneous azeotrope allowing removal of the first solvent and further wherein the second solvent is returned to the reactor.

In yet another embodiment, the urea is added to the polyol in a gradient method, as described in pending U.S. patent application Ser. No. 13/955,612, filed on Jul. 31, 2013, entitled "Process to Produce Polycarbamate Using a Gradient Feed of Urea," the disclosure of which is incorporated herein by reference in its entirety.

In certain embodiments, the process achieves at least a 50% conversion of hydroxyl groups of the polyol. All individual values and subranges from at least 50% conversion are included herein and disclosed herein; for example, the hydroxyl conversion may range from a lower limit of 50%, or in the alternative, the hydroxyl conversion may range from a lower limit of 55%, or in the alternative, the hydroxyl conversion may range from a lower limit of 60%, or in the alternative, the hydroxyl conversion may range from a lower limit of 65%, or in the alternative, the hydroxyl conversion may range from a lower limit of 70%, or in the alternative, the hydroxyl conversion may range from a lower limit of 75% or in the alternative, the hydroxyl conversion may range from a lower limit of 80%, or in the alternative, the hydroxyl conversion may range from a lower limit of 85%.

Trivalent Metal Catalysts

Catalysts included in embodiments of the inventive process are selected from the group consisting of: (i) compounds having the following formula $M_m Z_n$; wherein M is a trivalent metal, and Z is an anionic functionality or a functionality capable of forming a covalent bond with M and wherein n times a valence number of Z equals X and m times three equals Y wherein the absolute value of X equals the absolute value of Y.

Exemplary trivalent metals include Bismuth (III) ("Bi(III)"), Aluminum (III) ("Al(III)"), Ytterbium (III) ("Yb(III)"), Yttrium (III) ("Y(III)"), Iron (III) ("Fe(III)"), Lanthanum (III) ("La(III)"), Samarium (III) ("Sm(III)"), Ruthenium(III) ("Ru(III)"), Gallium (III) ("Ga(III)"), Scandium (III) ("Sc(III)") and Cerium (III) ("Ce(III)")

Exemplary Bi(III)-containing catalysts include Bismuth (III) trifluoromethanesulfonate, Bi(III) acetylacetonate, Bi(III) tri(2-ethylhexanoate), Bismuth (III) acetate, Bismuth (III) neodecanoate, Bismuth(III) oxide, Bismuth(III) chloride, Bismuth(III) bromide and triphenylbismuth.

Exemplary Al(III)-containing catalysts include Al(III) acetylacetonate, Al(III) isopropoxide, Aluminum oxide, Aluminum chloride, Aluminum bromide, Al(III) trifluoromethanesulfonate, Al(III) butoxide, and Al(III) tris(2-ethylhexanoate).

Exemplary Yb(III)-containing catalysts include Yb(III) trifluoromethanesulfonate, Yb(III) chloride, Yb(III) bromide, Yb(III) oxide, Yb(III) isopropoxide, Yb(III) acetylacetonate, Yb(III) 2,4-pentanedionate, Yb(III) 2-ethylhexanoate.

Exemplary Y(III)-containing catalysts include Y(III) trifluoromethanesulfonate, Y(III) acetylacetonate, Y(III) isopropoxide, Y(III) 2-ethylhexanoate, Y(III) oxide, Y(III) chloride and Y(III) bromide.

Exemplary Fe(III) catalysts include Fe(III) (acetylacetonate)$_3$, Fe(III) tris(2-ethylhexanoate), Fe(III) oxide, Fe(III) isopropoxide, Fe(III) chloride and Fe(III) bromide.

Exemplary La(III) catalysts include La(III) (acetylacetonate), La(III) chloride, La(III) bromide, La(III) trifluoromethanesulfonate, La(III) trifluoromethanesulfonate, La(III) isopropoxide, and La(III) oxide.

Exemplary Sm(III) catalysts include Sm(III) trifluoromethanesulfonate, Sm(III) acetylacetonate, Sm(III) isopropoxide, Sm(III) chloride, Sm(III) bromide, and Sm(III) oxide.

Exemplary Ru(III) catalysts include Ru(III) acetylacetonate, Ru(III) tri(2-ethylhexanoate), Ru(III) chloride, and Ru(III) bromide.

Exemplary Ga(III) catalysts include Tris(2,2,6,6,6)tetramethyl-3,5-heptanedionato)gallium(III).

Exemplary Sc(III) catalysts include Scandium (III) trifluoromethane sulfonate.

Exemplary Ce(III) catalysts include Cerium (III acetylacetonate, Cerium(III) 2-ethylhexanoate and cerium(III) trifluoromethane sulfonate.

Z is an anionic functionality or a functionality capable of forming a covalent bond with M. As can be seen from the foregoing examples, Z may be a combination of one or more anionic functionalities, one or more functionalities capable of forming a covalent bond with M, or a combination of anionic functionality(ies) and functionality(ies) capable of forming a covalent bond with M. In those instances where Z is a combination of more than one functionality, for example $Z1_{n1}Z2_{n2}$, one of ordinary skill in the art would understand that the absolute value of the sum of the valences times the appropriate n equals the absolute value of m times three. For example, if the catalyst has the formula $M_mZ1_{n1}Z2_{n2}$=FeOCl, then M=Fe(III), m=1, Z1=O with a valence of −2, Z2=Cl with a valence of −1, n1=1 and n2=1, such that m times 3=Y=3 and n1 time −2=−2 and n2 time −1=−1, and X=−2+−1=−3, and therefore the absolute values of Y and X are equal.

Exemplary components of the Z groups include 2-ethylhexanoate, benzoate, hexafluoroacetylacetonate, isopropoxide, acetyl acetonate, phenoxide, stearate, tert-butoxide, neodecanoate, citrate, trifluoromethane sulfonate, n-butoxide, trifluoroacetate, 1,1,1-trifluoro-2,4-pentanedionate, 2,2,6,6,-tetramethyl-3,5-hexanedionate, cresylate, ethoxide, methoxide, triethanolaminato, 2-methyl-2-butoxide, oxo, fluoride, chloride, bromide, iodide, aryl or substituted aryl or mixtures thereof and chelates thereof.

In one embodiment of the process, adding the urea to the polyol occurs in the presence of any one or more of the foregoing catalysts.

Additional Catalysts

In a certain embodiment of the process, adding the urea to the polyol occurs in the presence of one or more additional catalysts selected from the group consisting of carbamylation catalysts. Such second carbamylation catalysts include, for example, dibutyltin oxide, dibutyltin acetate, tetravalent metal based catalysts, such as Titanium (IV)-based compounds and Zirconium (IV)-based compounds, and divalent metal based catalysts, such as Manganese(II)-based compounds and Zinc (II)-based compounds.

By-Products

In an alternative embodiment, the instant invention provides a process, polycarbamate and coatings comprising the polycarbamate, in accordance with any of the preceding embodiments, except that a 100% solids product of the polycarbamate comprises less than 5 wt % total of biuret, cyanuric acid, and polyallophanate. All individual values and subranges from less than 5 wt % are included herein and disclosed herein; for example, the total amount of biuret, cyanuric acid, and polyallophanate in a 100 wt % solids polycarbamate product may be from an upper limit of 5 wt %, or in the alternative, from an upper limit of 4 wt %, or in the alternative, from an upper limit of 3 wt %, or in the alternative, from an upper limit of 2 wt %, or in the alternative, from an upper limit of 1 wt %, or in the alternative, from an upper limit of 0.5 wt %.

Coatings

The polycarbamate according to the embodiments disclosed herein may be used in coating compositions. Such coatings may include, for example, polyurethane from cross-linking reaction of the polycarbamate and components with multiple aldehyde functionalities. Exemplary end uses for such coatings include metal, ceramic, wood and plastic coatings, including for example wind blade coatings and automotive coatings.

EXAMPLES

The following examples illustrate the present invention but are not intended to limit the scope of the invention.

Inventive Example 1

Urea Addition to Polyol in the Presence of Al(III) Acetylacetonate

A 1-L reactor with heating mantle was used in the reaction. The reactor was equipped with an agitator, a thermal-couple and a nitrogen sparger. A water-cooled condenser was connected to the adaptor on the reactor lid. The overhead condensate was collected by a receiver and the non-condensable went through a bubbler filled with mineral oil and then entered a 1-L scrubber filled with water.

842.87 g PARALOID AU-608X polyol (commercially available from The Dow Chemical Company) which consists of 58% solid and 42% solvent (xylenes) was added to the reactor, which had 0.75 mol hydroxyl functionality. 6.65 g Al(III) acetylacetonate (99% pure) was added to the reactor. 45.49 g urea (99% pure) was used in this reaction. The heating mantle was started and set at 158° C. The nitrogen sparging flow rate was set at 20 sccm. The reaction mixture was agitated at 100 rpm and then adjusted to 400 rpm when the reactor temperature was over 60° C. When the reactor temperature reached 138° C., 30% of urea (13.65 g)

was added to the reactor. The reaction timer was also started. The urea was fed to the reactor in a semi-batch manner. The feeding rates are shown in Table 1.

TABLE 1

| Reaction Time (hr) | Urea mass (g) | Urea percentage (%) |
|---|---|---|
| 0 | 13.65 | 30% |
| 2 | 4.55 | 10% |
| 4 | 4.55 | 10% |
| 6 | 4.55 | 10% |
| 8 | 4.55 | 10% |
| 10 | 4.55 | 10% |
| 12 | 4.55 | 10% |
| 15 | 4.55 | 10% |

The reaction was carried out until the total reaction time reached 18 hours. The reaction temperature is between 138-142° C. After the reaction was complete, the heating mantle was shut down and the agitation rate was reduced to 60 rpm. When the reactor temperature dropped to 60° C., the polycarbamate product was poured out from the reactor. The final product was analyzed using $^{13}$C NMR. The hydroxyl conversion of the final product was 76.4%. The byproduct levels are shown in Table 2.

TABLE 2

| Biuret (wt % in 100% solids product) | Cyanuric Acid (wt % in 100% solids product) | Polyallophanate (wt % in 100% solids product) | Biuret + Cyanuric acid + polyallophate (wt % in 100% solids product) |
|---|---|---|---|
| 0.65% | 0.04% | 0.83% | 1.52% |

The final polycarbamate product color was Gardner level 3.

Inventive Example 2

Urea Addition to Polyol in the Presence of Al(III) Isopropoxide

A 1-L reactor with heating mantle was used in the reaction. The reactor was equipped with an agitator, a thermal-couple and a nitrogen sparger. A water-cooled condenser was connected to the adaptor on the reactor lid. The overhead condensate was collected by a receiver and the non-condensable went through a bubbler filled with mineral oil and then entered a 1-L scrubber filled with water.

884.49 g PARALOID AU-608X polyol which consists of 58% solid and 42% solvent (xylenes) was added to the reactor, which had 0.79 mol hydroxyl functionality. 4.35 g Al(III) isopropoxide (98% pure) was added to the reactor. 40.57 g urea (99% pure) was used in this reaction. The heating mantle was started and set at 158° C. The nitrogen sparging flow rate was set at 20 sccm. The reaction mixture was agitated at 100 rpm and then adjusted to 400 rpm when the reactor temperature was over 60° C. 47.1% of Urea (19.09 g) was added to the reactor when the reactor temperature reached 138° C. and the reaction timer was started. The reaction was carried out between 138-142° C. When the reaction time reached 4 hours, 29.4% urea (11.93 g) was added to the reactor. When the reaction time reached 7 hours, the rest 23.5% urea (9.55 g) was added to the reactor. The total reaction time was 13 hours. The reaction temperature is between 138-142° C. After the reaction was complete, the heating mantle was shut down and the agitation rate was reduced to 60 rpm. When the reactor temperature dropped to 60° C., the polycarbamate product was poured out from the reactor. The final product was analyzed using $^{13}$C NMR. The hydroxyl conversion of the final product was 44.0%. The byproduct levels are shown in Table 3.

TABLE 3

| Biuret (wt % in 100% solids product) | Cyanuric Acid (wt % in 100% solids product) | Polyallophanate (wt % in 100% solids product) | Biuret + Cyanuric acid + polyallophate (wt % in 100% solids product) |
|---|---|---|---|
| 0.50% | 0.05% | 1.24% | 1.79% |

The final polycarbamate product color was Gardner level 3.

Comparative Example-1

Methyl Carbamate Addition to Polyol in the Presence of Al(III) Acetylacetonate

A 1-L reactor with heating mantle was used in the reaction. The reactor was equipped with an agitator, a thermal-couple and a nitrogen sparger. A heated condenser was connected to the adaptor on the reactor lid. A heating batch equipped with a circulation pump was used to heat water circulating in the condenser. The overhead condensate was collected by a receiver and the non-condensable went through a bubbler filled with mineral oil and then entered a 1-L scrubber filled with water.

877.91 g PARALOID AU-608X polyol which consists of 58% solid and 42% solvent (xylenes) was added to the reactor, which had 0.78 mol hydroxyl functionality. 13.86 g Al(III) acetylacetonate (99% pure) was added to the reactor. The heating mantle was started and set at 158° C. The heating batch for the overhead condenser was set at 70° C. The nitrogen sparging flow rate was set at 20 sccm. The reaction mixture was agitated at 100 rpm and then adjusted to 400 rpm when the reactor temperature was over 60° C. When the reactor temperature reached 70° C., 59.82 g (98% pure) methyl carbamate was added to the reactor. When the reactor temperature reached 138° C., the reaction timer was started.

The total reaction time was 20 hours. The reaction temperature is between 138-142° C. After the reaction was complete, the heating mantle was shut down and the agitation rate was reduced to 60 rpm. When the reactor temperature dropped to 60° C., the polycarbamate product was poured out from the reactor. The final product was analyzed using $^{13}$C NMR. The hydroxyl conversion of the final product was 53.6%.

Inventive Example 3

Urea Addition to Polyol in the Presence of Bismuth (III) Trifluoromethanesulfonate A 1-L reactor with heating mantle was used in the reaction. The reactor was equipped with an agitator, a thermal-couple and a nitrogen sparger. A water-cooled condenser was connected to the adaptor on the reactor lid. The overhead condensate was collected by a receiver and the non-condensable went through a bubbler filled with mineral oil and then entered a 1-L scrubber filled with water.

767.57 g PARALOID AU-608X polyol which consists of 58% solid and 42% solvent (xylenes) was added to the reactor, which had 0.68 mol hydroxyl functionality. 6.2 g Bismuth (III) Trifluoromethanesulfonate (99% pure) was added to the reactor. The heating mantle was started and set at 158° C. The nitrogen sparging flow rate was set at 20 sccm. The reaction mixture was agitated at 100 rpm and then adjusted to 400 rpm when the reactor temperature was over 60° C. When the reactor temperature reached 138° C., 41.42 g urea (99% pure) was added to the reactor. The reaction timer was also started.

The total reaction time was 12.5 hours. The reaction temperature is between 138-142° C. After the reaction was complete, the heating mantle was shut down and the agitation rate was reduced to 60 rpm. When the reactor temperature dropped to 60° C., the polycarbamate product was poured out from the reactor. The final product was analyzed using $^{13}C$ NMR. The hydroxyl conversion of the final product was 77.8%. The byproduct levels are shown in Table 4.

TABLE 4

| Biuret (wt % in 100% solids product) | Cyanuric Acid (wt % in 100% solids product) | Polyallophanate (wt % in 100% solids product) | Biuret + Cyanuric acid + polyallophate (wt % in 100% solids product) |
| --- | --- | --- | --- |
| 0.64% | 0.05% | 1.12% | 1.81% |

The final polycarbamate product color was Gardner level 4.

Inventive Example-4

Urea Addition to Polyol in the Presence of Bismuth (III) Trifluoromethanesulfonate A 1-L reactor with heating mantle was used in the reaction. The reactor was equipped with an agitator, a thermal-couple and a nitrogen sparger. A water-cooled condenser was connected to the adaptor on the reactor lid. The overhead condensate was collected by a receiver and the non-condensable went through a bubbler filled with mineral oil and then entered a 1-L scrubber filled with water.

793.2 g PARALOID AU-608X polyol which consists of 58% solid and 42% solvent (xylenes) was added to the reactor, which had 0.71 mol hydroxyl functionality. The heating mantle was started and set at 158° C. The nitrogen sparging flow rate was set at 20 sccm. The reaction mixture was agitated at 100 rpm and then adjusted to 400 rpm when the reactor temperature was over 60° C.

6.33 g Bismuth (III) Trifluoromethanesulfonate (99% pure) and 42.81 g urea (99% pure) were used for this reaction. Both urea solid and catalyst (Bismuth (III) Trifluoromethanesulfonate) were both added to the reactor in a semi-batch manner. When the reactor temperature reached 138° C., the addition of urea and catalyst was started and the reaction timer was started. The additions of catalyst and urea are shown in Tables 5 and 6:

TABLE 5

| Reaction time (hour) | Catalyst (g) | Catalyst Percentage (%) |
| --- | --- | --- |
| 0 | 3.17 | 50% |
| 3 | 1.58 | 25% |
| 5 | 1.58 | 25% |

TABLE 6

| Reaction time (hour) | Urea (g) | Urea Percentage (%) |
| --- | --- | --- |
| 0 | 21.40 | 50% |
| 3 | 5.35 | 12.50% |
| 5 | 5.35 | 12.50% |
| 9 | 5.35 | 12.50% |
| 12 | 5.35 | 12.50% |

The total reaction time was 20 hours. The reaction temperature is between 138-142° C. After the reaction was complete, the heating mantle was shut down and the agitation rate was reduced to 60 rpm. When the reactor temperature dropped to 60° C., the polycarbamate product was poured out from the reactor. The final product was analyzed using $^{13}C$ NMR. The hydroxyl conversion of the final product was 88.8%. The byproduct levels are shown in Table 7.

TABLE 7

| Biuret (wt % in 100% solids product) | Cyanuric Acid (wt % in 100% solids product) | Polyallophanate (wt % in 100% solids product) | Biuret + Cyanuric acid + polyallophate (wt % in 100% solids product) |
| --- | --- | --- | --- |
| 0.30% | 0.04% | 0.76% | 1.11% |

The final polycarbamate product color was Gardner level 4.

Inventive Example 5

Urea Addition to Polyol in the Presence of Bi(III)Trifluoromethanesulfonate

A 1-L reactor with heating mantle was used in the reaction. The reactor was equipped with an agitator, a thermal-couple and a nitrogen sparger. A water-cooled condenser was connected to the adaptor on the reactor lid. The overhead condensate was collected by a receiver and the non-condensable went through a bubbler filled with mineral oil and then entered a 1-L scrubber filled with water.

579.94 g PARALOID AU-608X polyol which consists of 58% solid and 42% solvent (xylenes) was added to the reactor, which had 0.52 mol hydroxyl functionality. The heating mantle was started and set at 158° C. The nitrogen sparging flow rate was set at 20 sccm. The reaction mixture was agitated at 100 rpm and then adjusted to 400 rpm when the reactor temperature was over 60° C.

4.63 g Bismuth (III) Trifluoromethanesulfonate (99% pure) was used as the catalyst for this reaction. The catalyst was added to the reactor in a semi-batch manner as shown below. 31.30 g urea (99% pure) was dissolved in 29.0 g deionized water to form aqueous solution. The urea solution was fed into the reactor using a syringe pump in a semi-batch manner. When the reactor temperature reached 138° C., the additions of both catalyst and urea solution were started and the reaction timer was started. The initial syringe pump rate was set at 2 ml/min for 10 minutes to feed about 30% of the total urea solution. Then the pump rate was reduced to 5 ml/hr to feed the rest 70% solution. The total feeding time was about 10 hours. The rate of addition of catalyst is shown in Table 8.

TABLE 8

| Reaction time (hour) | Catalyst (g) | Catalyst Percentage (%) |
| --- | --- | --- |
| 0 | 2.32 | 50% |
| 3 | 1.16 | 25% |
| 5 | 1.16 | 25% |

After the urea feeding was done, the reaction was continued to reach total reaction time of 15 hours. The reaction temperature is between 138-142° C. After the reaction was complete, the heating mantle was shut down and the agitation rate was reduced to 60 rpm. When the reactor temperature dropped to 60° C., the polycarbamate product was poured out from the reactor. The final product was analyzed using $^{13}$C NMR. The hydroxyl conversion of the final product was 67.2%. The byproduct levels are shown in Table 9.

TABLE 9

| Biuret (wt % in 100% solids product) | Cyanuric Acid (wt % in 100% solids product) | Polyallophanate (wt % in 100% solids product) | Biuret + Cyanuric acid + polyallophate (wt % in 100% solids product) |
| --- | --- | --- | --- |
| 0.54% | 0.03% | 0.59% | 1.16% |

The final polycarbamate product color was Gardner level 4.

Inventive Example-6

Urea Addition to Polyol in the Presence of Bi(III) 2-Ethylhexanoate

A 1-L reactor with heating mantle was used in the reaction. The reactor was equipped with an agitator, a thermal-couple and a nitrogen sparger. A water-cooled condenser was connected to the adaptor on the reactor lid. The overhead condensate was collected by a receiver and the non-condensable went through a bubbler filled with mineral oil and then entered a 1-L scrubber filled with water.

777.48 g PARALOID AU-608X polyol which consists of 58% solid and 42% solvent (xylenes) was added to the reactor, which had 0.69 mol hydroxyl functionality. 11.97 g Bismuth (III) 2-ethylhexanoate (99% pure) was added to the reactor. The heating mantle was started and set at 158° C. The nitrogen sparging flow rate was set at 20 sccm. The reaction mixture was agitated at 100 rpm and then adjusted to 400 rpm when the reactor temperature was over 60° C.

35.66 g urea (99% pure) was used for this reaction. The urea solid was fed into the reactor using a semi-batch manner. When the reactor temperature reached 138° C., the additions of urea were started and the reaction timer was started. The addition of urea is shown in Table 10:

TABLE 10

| Reaction time (hour) | Urea (g) | Urea Percentage (%) |
| --- | --- | --- |
| 0 | 16.78 | 47.1% |
| 4 | 10.49 | 29.4% |
| 7 | 8.39 | 23.5% |

After the urea feeding was done, the reaction was continued to reach total reaction time of 13 hours. The reaction temperature is between 138-142° C. After the reaction was complete, the heating mantle was shut down and the agitation rate was reduced to 60 rpm. When the reactor temperature dropped to 60° C., the polycarbamate product was poured out from the reactor. The final product was analyzed using $^{13}$C NMR. The hydroxyl conversion of the final product was 78.0%. The byproduct levels are shown in Table 11.

TABLE 11

| Biuret (wt % in 100% solids product) | Cyanuric Acid (wt % in 100% solids product) | Polyallophanate (wt % in 100% solids product) | Biuret + Cyanuric acid + polyallophate (wt % in 100% solids product) |
| --- | --- | --- | --- |
| 0.20% | 0.00% | 0.28% | 0.48% |

The final polycarbamate product color was Gardner level 4.

Inventive Example 7

Urea Addition to Polyol in the Presence of Bi(III) 2-Ethylhexanoate

A 1-L reactor with heating mantle was used in the reaction. The reactor was equipped with an agitator, a thermal-couple and a nitrogen sparger. A water-cooled condenser was connected to the adaptor on the reactor lid. The overhead condensate was collected by a receiver and the non-condensable went through a bubbler filled with mineral oil and then entered a 1-L scrubber filled with water.

863.31 g PARALOID AU-608X polyol which consists of 58% solid and 42% solvent (xylenes) was added to the reactor, which had 0.77 mol hydroxyl functionality. 13.29 g Bismuth (III) 2-ethylhexanoate (99% pure) was added to the reactor. The heating mantle was started and set at 158° C. The nitrogen sparging flow rate was set at 20 sccm. The reaction mixture was agitated at 100 rpm and then adjusted to 400 rpm when the reactor temperature was over 60° C.

41.0 g urea (99% pure) was used dissolved in 38.0 g deionized water to form aqueous solution. The urea solution was fed into the reactor in a semi-batch manner using a syringe pump. When the reactor temperature reached 138° C., the additions of urea were started and the reaction timer was started. The initial urea feeding rate was set at 2 ml/min to feed 30% of the urea solution. The feeding rate was then adjusted to 5 ml/hr to feed the rest 70% of urea solution. The urea feeding lasted for about 10 hours.

After the urea feeding was done, the reaction was continued to reach total reaction time of 16 hours. The reaction temperature is between 138-142° C. After the reaction was complete, the heating mantle was shut down and the agitation rate was reduced to 60 rpm. When the reactor temperature dropped to 60° C., the polycarbamate product was poured out from the reactor. The final product was analyzed using $^{13}$C NMR. The hydroxyl conversion of the final product was 70.8%. The byproduct levels are shown in Table 12.

TABLE 12

| Biuret (wt % in 100% solids product) | Cyanuric Acid (wt % in 100% solids product) | Polyallophanate (wt % in 100% solids product) | Biuret + Cyanuric acid + polyallophate (wt % in 100% solids product) |
|---|---|---|---|
| 0.15% | 0.01% | 0.18% | 0.34% |

The final polycarbamate product color was Gardner level 4.

High Throughput Examples

Carbamylation reactions of an acrylic polyol (PARALOID AU608x) using both methyl carbamate and urea were carried out in an array of 48 high throughput reactors with an internal volume of 35 mL (utilizing glass tube inserts), equipped with stirring and capable of continuous nitrogen purge of the reactor head space to remove the volatile by products (ammonia gas).

A comprehensive list of compounds based on different metals and ligands was tested in this study. Experiments were carried out in sets of 48 in triplicates. Each set of 48 contained four experiments using dibutyltin oxide and two experiments with no catalyst, as control experiments. Pre-weighed glass tubes were loaded with about 9 g of a 65% solution of Au608x polyol in xylene. They were then weighed to determine the exact weight of polyol added. Urea and catalyst were then added based on the weight of the polyol in order to achieve a molar (urea/OH) ratio of 0.6 and hydroxyl groups and 1 wt % of catalyst, based on the weight of polyol; respectively. The tubes were then placed into the bottom part of the high throughput reactor. The reactor head was placed on top and clamped in order to seal the reactor. The reactor was then heated to 140° C. while being purged by nitrogen.

FT-IR was used to monitor the disappearance of hydroxyl group as a measure of the extent of each reaction. The experiments that were conducted with dibutyltin oxide, $Bu_2SnO$, in each set of 48 were used as reference for comparing the efficiency of the each compound in catalyzing the carbamylation reaction, within that set. The extent of reaction in each tube, as determined by FT-IR, was divided by the average of the extent of reaction utilizing $Bu_2SnO$ in that set. This was to block the potential set-to-set variability in the experiments that might have existed.

Relative conversion data for the carbamylation experiments, including the results of the "no catalyst" reactions, are provided in Table 13.

TABLE 13

| Catalyst | Relative Conversion |
|---|---|
| Yttrium trifluoromethane sulfonate | 0.99 |
| Aluminum tert-butoxide | 0.81 |
| Ytterbium trifluoromethane sulfonate | 0.93 |
| Aluminum 2-ethylhexanoate, basic | 0.95 |
| Triphenylbismuth | 1.08 |
| Lanthanum trifluroacetate | 1.03 |
| lanthanum (III) acetylacetonate | 0.95 |
| Aluminum i-propoxide | 0.98 |
| bismuth 2-ethylhexanoate | 0.97 |
| lanthium(III) trifluoromethane sulfonate | 0.98 |
| Bismuth benzoate | 1.02 |
| Yttrium trifluoroacetate | 1.00 |
| yttrium(III) hexafluoroacetylacetonate | 0.98 |

TABLE 13-continued

| Catalyst | Relative Conversion |
|---|---|
| Scandium trifluoromethane sulfonate | 1.08 |
| cerium(III) trifluoromethane sulfonate | 0.95 |
| Bismuth(III) citrate | 0.91 |
| Aluminum benzoate | 0.86 |
| Tris(2,2,6,6)tetramethyl-3,5-heptanedionato)gallium(III) | 1.24 |
| Lanthanum(III) 2-ethylhexanoate | 1.10 |
| Aluminum acetylacetonate | 1.04 |
| Lanthanum(III) i-propoxide | 0.96 |
| Yttrium(III) neodecanoate | 1.01 |
| Cerium Acetyl Acetonate | 1.01 |
| Tris(2,2,6,6-tetramethyl-3,5-hetanedionato) lanthanum(III) | 0.83 |
| Bismuth (III) acetate | 1.11 |
| Aluminum phenoxide | 0.89 |
| Aluminum hexafluoroacetylacetonate | 0.88 |
| Tris(2,2,6,6-tetramethyl-3,5-heptanedionato) aluminum [Al(TMHD)3] | 0.92 |
| Tris(2,2,6,6-tetramethyl-3,5-heptanedionato)yttrium(III) ( | 0.88 |
| Aluminum Stearate | 0.93 |
| Yttrium(III) 2-ethylhexanoate | 0.95 |
| Bismuth neodecanoate | 1.04 |
| Aluminum Stearate monobasic grade | 0.93 |
| bismuth (III) trifluoromethane | 0.77 |
| Triphenylbismuth dichloride | 1.08 |
| Yttrium (III) acetylacetonate hydrate | 0.98 |
| Yttrium(III) i-propoxide | 0.89 |
| methylaluminum bis(2,6-di-tert-butyl-4-methylphonoxide | 0.88 |
| Cerium(III) 2-ethylhexanoate 49% in 2-ethylhexanoic acid | 0.97 |
| $Bu_2SnO$ | 1.01 |
| $Bu_2SnO$ | 1.01 |
| $Bu_2SnO$ | 0.99 |
| $Bu_2SnO$ | 0.99 |
| No catalyst | 0.59 |
| No catalyst | 0.54 |

Test Methods

OH Number Titration

OH number is the magnitude of the hydroxyl number for a polyol as expressed in terms of milligrams potassium hydroxide per gram of polyol (mg KOH/g polyol). Hydroxyl number (OH #) indicates the concentration of hydroxyl moieties in a composition of polymers, particularly polyols. The hydroxyl number for a sample of polymers is determined by first titrating for the acid groups to obtain an acid number (mg KOH/g polyol) and secondly, acetylation with pyridine and acetic anhydride in which the result is obtained as a difference between two titrations with potassium hydroxide solution, one titration with a blank for reference and one titration with the sample. A hydroxyl number is the weight of potassium hydroxide in milligrams that will neutralize the acetic anhydride capable of combining by acetylation with one gram of a polyol plus the acid number from the acid titration in terms of the weight of potassium hydroxide in milligrams that will neutralize the acid groups in the polyol. A higher hydroxyl number indicates a higher concentration of hydroxyl moieties within a composition. A description of how to determine a hydroxyl number for a composition is well-known in the art, for example in Woods, G., The ICI Polyurethanes Book, $2^{nd}$ ed. (ICI Polyurethanes, Netherlands, 1990).

Gardner color: was measured according to ASTM D1544 "Standard Test Method for Color of Transparent Liquids (Gardner Color Scale)" using a HunterLab colorimeter.

$^{13}C$ NMR: All samples were characterized by $^{13}C$ NMR in solutions. For a typical sample preparation, 0.6 g dry material was dissolved in 2.5 mL DMSO-$d_6$ solvent at room temperature in a glass vial. The DMSO-$d_6$ solvent contains 0.015 M Cr(acac)$_3$ as a relaxation agent. The solution was then transferred to a 10 mm NMR tube for characterization. Quantitative inverse-gated $^{13}$C NMR experiments were performed on a Bruker Avance 400 MHz ($^1$H frequency) NMR spectrometer equipped with a 10 mm DUAL C/H cryoprobe. All experiments were carried out without sample spinning at 25.0° C. Calibrated 90° pulse was applied in the inverse-gated pulse sequence. The relaxation delay between consecutive data acquisitions is 5*$T_1$, where $T_1$ is the longest spin-lattice relaxation time of all nuclei in the measured system. The $^{13}$C NMR spectra were processed with a line broadening of 1 Hz, and referenced to 39.5 ppm for the DMSO-$d_6$ resonance peak.

Information that can be obtained from $^{13}$C NMR spectra includes the percent of hydroxyl conversion, byproduct levels and solid content of the reaction product. The carbon next to a hydroxyl group has a chemical shift change after the carbamylation reaction. The hydroxyl conversion was calculated from the peak intensity ratio of the carbon after and before a carbamylation reaction. In a quantitative $^{13}$C NMR spectrum, each component of the measured system has a unique resonance peak, and its peak intensity is proportional to the molar concentration of that species. The byproduct levels and solid content were calculated by integrating the desired peaks. The molar concentration can be converted to weight percentage if the molecular weights for all species are known. In calculating the solid content, any components other than known solvents are classified as solid.

The present invention may be embodied in other forms without departing from the spirit and the essential attributes thereof, and, accordingly, reference should be made to the appended claims, rather than to the foregoing specification, as indicating the scope of the invention.

We claim:

1. A process to prepare polycarbamate comprising:
    adding urea to a polyol in the presence of at least one catalyst selected from the group consisting of Al(III) acetylacetonate, Bi (III) tritfluoromethanesulfonate, and Bi(III) tri(2-ethylhexanoate), wherein the process exhibits equal to or greater than 50% hydroxyl conversion at a reaction time between 10 and 20 hours.

2. The process according to claim 1, wherein a second catalyst selected from the group consisting of carbamylation catalysts is present.

3. The process according to claim 2, wherein the second catalyst is dibutyltin oxide and/or dibutyltin acetate.

* * * * *